(12) United States Patent  (10) Patent No.: US 8,545,469 B2
Andresen et al.  (45) Date of Patent: Oct. 1, 2013

(54) COMPONENT FOR SECURING ATTACHMENT OF A MEDICAL DEVICE TO SKIN

(75) Inventors: Angelica Andresen, Torslanda (SE); Dennis Hansson, Gunnilse (SE); Eva-Karin Daun, Lerum (SE); Charlotta Strandeberg, Gothenburg (SE)

(73) Assignee: Mölnlycke Health Care AB, Göteborg (SE)

( * ) Notice: Subject to any disclaimer, the term of this patent is extended or adjusted under 35 U.S.C. 154(b) by 85 days.

(21) Appl. No.: 13/057,571

(22) PCT Filed: Jul. 6, 2009

(86) PCT No.: PCT/SE2009/050877
§ 371 (c)(1),
(2), (4) Date: Feb. 4, 2011

(87) PCT Pub. No.: WO2010/016791
PCT Pub. Date: Feb. 11, 2010

(65) Prior Publication Data
US 2011/0137271 A1  Jun. 9, 2011

(30) Foreign Application Priority Data
Aug. 5, 2008  (SE) .................................. 0801761-8

(51) Int. Cl.
*A61F 5/44*  (2006.01)
(52) U.S. Cl.
USPC .......................................... 604/344; 604/338
(58) Field of Classification Search
USPC .......... 604/304, 307, 313, 319, 323, 332–344
See application file for complete search history.

(56) References Cited

U.S. PATENT DOCUMENTS 3,572,340 A   3/1971 Lloyd
4,535,819 A * 8/1985 Atkinson et al. .............. 137/846
(Continued)

FOREIGN PATENT DOCUMENTS

CN         1874806      6/2005
DE   202005019670 U1   4/2006
(Continued)

OTHER PUBLICATIONS

Mirriam-Webster, "affix," Retrieved Dec. 28, 2012, http://www.merriam-webster.com/dictionary/affix.*

(Continued)

*Primary Examiner* — Loan Thanh
*Assistant Examiner* — Jennifer M Deichl
(74) *Attorney, Agent, or Firm* — Ballard Spahr LLP

(57) ABSTRACT

A component for securing attachment of a medical device, such as a wound dressing or an ostomy bag is disclosed, to the skin of a patient, said component including a first plastic film coated with a skin-friendly adhesive on the lower side thereof. According to the invention a body of soft, compressible and elastic material is disposed between the first plastic film and a second plastic film, said first and second films extending beyond the compressible body around the circumference thereof and are affixed to each other in parts extending around the circumference of the compressible body so that a closed space containing said compressible body is formed, said closed space being in contact with the surrounding atmosphere by a non-return valve, and in that the first plastic film includes through-going openings in a region delimited by the compressible body.

11 Claims, 3 Drawing Sheets

(56) References Cited

U.S. PATENT DOCUMENTS

| | | | |
|---|---|---|---|
| 4,596,566 A * | 6/1986 | Kay | 604/343 |
| 5,540,922 A | 7/1996 | Fabo | |
| 5,635,201 A | 6/1997 | Fabo | |
| 6,071,267 A | 6/2000 | Zamierowski | |
| 6,635,050 B1 * | 10/2003 | Jensen et al. | 606/1 |
| 7,172,581 B2 * | 2/2007 | Ciok et al. | 604/339 |
| 7,976,522 B2 * | 7/2011 | Hansen et al. | 604/338 |
| 2001/0029956 A1 | 10/2001 | Argenta et al. | |
| 2001/0043943 A1 | 11/2001 | Coffey | |
| 2007/0027414 A1 | 2/2007 | Hoffman et al. | |
| 2007/0167926 A1 * | 7/2007 | Blott et al. | 604/304 |
| 2008/0167593 A1 | 7/2008 | Fleischmann | |
| 2008/0287892 A1 * | 11/2008 | Khan et al. | 604/313 |
| 2008/0306456 A1 | 12/2008 | Riesinger | 604/316 |
| 2009/0012441 A1 * | 1/2009 | Mulligan | 602/57 |

FOREIGN PATENT DOCUMENTS

| | | |
|---|---|---|
| DE | 102005007016 A1 | 8/2006 |
| EP | 0300620 A1 | 1/1989 |
| WO | WO 2005/051461 | 6/2005 |
| WO | WO-2005051461 A1 | 6/2005 |
| WO | WO 2007/068477 | 6/2007 |

OTHER PUBLICATIONS

International Search Report with Written Opinion mailed on Oct. 23, 2009 for Intl. App. No. PCT/SE2009/050877, filed on Jul. 6, 2009 (Inventor—Andresen et al.; Applicant—Molnlycke Health Care AB; pp. 1-11).

International Preliminary Report on Patentability issued on Feb. 8, 2011 for Intl. App. No. PCT/SE2009/050877, filed on Jul. 6, 2009 (Inventor—Andresen et al.; Applicant—Molnlycke Health Care AB; pp. 1-7).

* cited by examiner

COMPONENT FOR SECURING ATTACHMENT OF A MEDICAL DEVICE TO SKIN

CROSS REFERENCE TO RELATED APPLICATIONS

The present application is a National Phase Application of International Application No. PCT/SE2009/050877, filed Jul. 6, 2009, which claims priority to Swedish Patent Application No. 0801761-8, filed Aug. 5, 2008, which applications are incorporated herein fully by this reference.

TECHNICAL FIELD

The present invention relates to a component for securing attachment of a medical device, such as a wound dressing or an ostomy bag, to the skin of a patient, said component including a first plastic film coated with an adhesive on the lower side thereof, i.e. the side facing the skin when the component is used.

BACKGROUND OF THE INVENTION

A principal function of the adhesive coating on said component is to attach the component tightly to the skin of the patient, so that the fluid-borne transport of bacteria between the skin and the adhesive coating is prevented, and to attach the component securely to the skin, so that the medical device, such as a wound dressing or an ostomy bag, remains in place during all the normal loadings to which it is subjected. Currently used adhesives for such components attach well to dry skin but have a tendency to unstuck on moist skin. It is therefore a problem to secure wound dressings or other medical devices to moist areas on the skin of the human body, such as the armpits, the groin and sacrum. If the skin is damaged the moist level will increase thereby increasing the risk for the wound dressing or other medical device to unstuck.

A way of solving the problem with moist skin is to use adhesives attaching such components very hard to the skin. However, such adhesives often attach themselves to the skin so strongly that parts of the Stratum Corneum, that is to say the uppermost layer of the skin, become stuck to the adhesive and are pulled away from the skin when the film dressing is loosened. This can lead to irritation of and damage to the skin.

A first objective of the invention is to improve a component of the kind stated in the introductory paragraph of the description so that the force with which it is attached to the skin of a user can be increased if desired. A further object is that the adhesive used on such components should permit removal of the above mentioned component without causing damage to the skin or pain to the patient.

SUMMARY OF THE INVENTION

The first objective is accomplished by a component for securing attachment of a medical device, such as a wound dressing or an ostomy bag, to the skin of a patient, said component including a first plastic film coated with a skin-friendly adhesive on the lower side thereof, i.e. the side facing the skin when the component is used, characterised in that an annular body of soft, compressible and elastic material is disposed between the first plastic film and a second plastic film, said first and second films extending beyond the compressible body around the inner and outer circumferences thereof and are affixed to each other in parts extending around the inner and outer circumferences of the compressible body so that a closed space containing said compressible body is formed, said closed space being in contact with the surrounding atmosphere by a non-return valve, and in that the first plastic film includes through-going openings in a region delimited by the compressible body. When such a component is attached to the skin of a patient, pressing on the compressible body will force air out of the closed space containing the body through the non-return valve and a sub-pressure will be created in said closed space. This sub-pressure will also be present beneath the through-going openings in the first plastic film in the region delimited by said compressible body. It is of course also possible to create said sub-pressure and thereby an additional holding force by sucking air out of the compressible body by a manual pump or other source of sub-pressure.

In a preferred embodiment, said compressible body is made of polymer foam, preferably polyurethane foam.

Said non-return valve can consist of a tube of flexible material with one end connected to the space between the first and second films containing said compressible body and the opposite end connected to the atmosphere, said tube being collapsed in a relaxed condition so that the interior of the upper and lower sides of said tube abut each other in the relaxed condition but will be distanced from each other by the over-pressure created by compressing said compressible body.

Alternatively a pump for creating sub-pressure can be connected to the closed space containing the compressible body, the non-return valve then being connected to the outlet of said pump.

In a second alternative said non-return valve can be present in a line leading from the closed spaced containing said compressible body to the surrounding atmosphere, the outer end of said line being connectable to a source of sub-pressure.

The through-going openings in said region delimited by said compressible body can be arranged in a pattern of perforations evenly distributed in said region.

The adhesive layer is preferably a tacky silicone gel. Such an adhesive is skin-friendly and will allow removal of the component without causing pain to the user. Since a silicone gel by definition is soft, it will penetrate into any unevenness in the skin, thereby to a high degree reduce the risk for air to leak into said closed space which means that the created sub-pressure and thereby the holding force created in the region of said through-going openings, which is added to the attachment force of the adhesive, will remain during a long period of time Preferably, a layer of release material covers the adhesive layer before use of the component.

BRIEF DESCRIPTION OF THE DRAWING

The invention will now be described with reference to the enclosed figures, of which.

DESCRIPTION OF EMBODIMENTS

Figure 1:
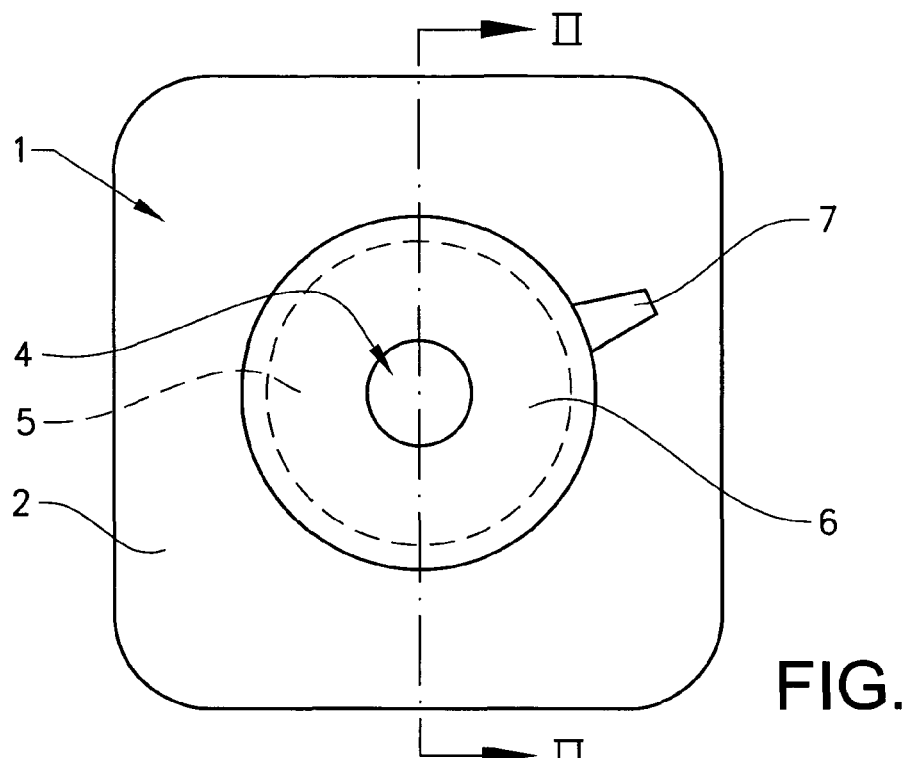
FIG. 1 schematically discloses a top plan view of a component according to a first preferred embodiment of the present invention, FIG. 2 discloses a cross-sectional view along line II-II in FIG. 1, FIG. 3 discloses a plan view from the lower side of the component according to FIG. 1, FIGS. 4 and 5 illustrate a method of measuring softness.
Figure 2:
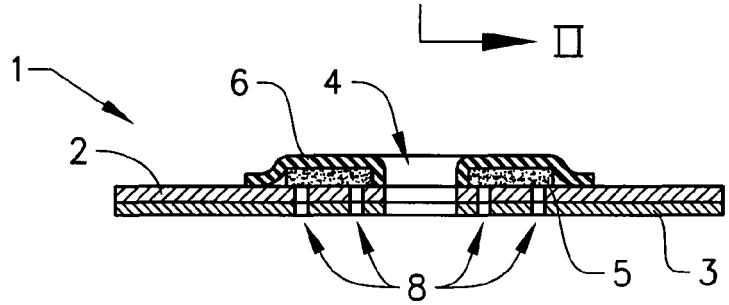
Figure 3:
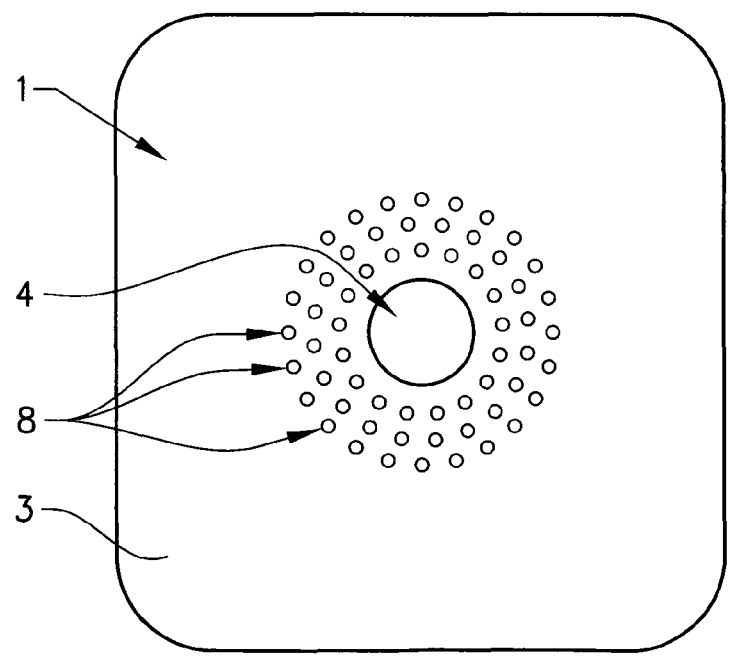

A first preferred embodiment of a component 1 for facilitating attachment of an ostomy bag to the body of a patient is schematically disclosed in FIGS. 1-3. Component 1 includes a first plastic film 2 coated with a layer 3 of a skin-friendly adhesive on the lower side thereof, i.e. the side facing the skin when the component 1 is used, and also a hole 4 in the middle portion of the component, as is usual for such components. An annular body 5 of soft, compressible and elastic material is surrounding hole 4 and a second plastic film 6 covers the compressible body 5. The second plastic film 6 is affixed to the first plastic film around the inner and outer perimeters of the compressible body 5 in an air-tight manner by any suitable means, such as a weld or a glue seam. Thereby a closed space containing the compressible body 5 is formed between the first and second plastic films 2,6. Said closed space is connectable to surrounding atmosphere by a non-return valve 7, which allows air flowing out of the closed space but not air flowing in. Furthermore, the first plastic film 2 and the layer of skin-friendly adhesive 3 includes through-going openings 8 in a region delimited by the outer and inner perimeters of the compressible body 5.

Before use of the component 1 the adhesive layer 3 is covered by a release paper or the like (not shown) which is removed before applying the component.

The aim of the component 1 is to create a holding force for the component which force in an easy way can be added to the adhesive holding force of the skin-friendly adhesive in layer 3. This is accomplished by a user of the component simply by pressing on the compressible body 5 after the component has been put on place on the skin of the user. By pressing on the body 5, air will be pressed out of the body and out of the closed space containing said body through the non-return valve 7. A sub-pressure will then be created in said closed space.

The skin of the user is in communication with the closed space through each of the openings 8 in the region delimited by the outer and inner perimeters of the compressible body 5. By the use of a skin-friendly adhesive enabling removal of a component attached to the skin without causing pain to the user, it is also ensured that air will not leak in beneath the adhesive layer since a skin-friendly adhesive fills wrinkles and other unevenness in the skin, thereby creating an air-tight barrier. The sub-pressure in the closed space containing the compressed body 5 will thus be maintained and will act on the skin through the openings 8, thereby creating a holding force in said region additional to the holding force of the adhesive layer 3.

The plastic films 2,6 are preferably of polyurethane and have a thickness of 10-100 μm, preferably 10-50 μm. Other plastic materials such as polyethylene, polypropylene or polyester could also be used. Films 2,6 are preferably of the same material even if this is not necessary.

The compressible body 5 is made of polymer foam, preferably of polyurethane foam, but other foam materials, such as natural sponges or other foamed plastic materials can be used. In addition to foams other compressible and resilient material having air-filled voids in expanded condition can also be used.

The adhesive layer 3 consists preferably of a tacky silicone gel. Silicone gel is very soft and possesses low surface energy, and it adapts very well to the skin, that is to say it flows out into any unevenness in the skin and creates a large contact surface between the skin and the silicone gel. This large contact surface helps the silicone gel to become attached securely to the skin, in spite of the fact that the strength of the adhesive attachment of the silicone gel to the skin is not in itself so strong. Moreover, hard adhesives often attach themselves to the skin so strongly that parts of the Stratum Corneum, that is to say the uppermost layer of the skin, become stuck to the adhesive and are pulled away from the skin when the film dressing is loosened. This can lead to irritation of and damage to the skin. By the use of a soft adhesive removal of the component can be made without causing pain to the user Suitable soft, skin friendly adhesives for the adhesive layer 3 are for example addition curing RTV (Room Temperature Vulcanizing) silicone systems which after mixing crosslink and form a self-adhering gel. Examples of such RTV silicone systems are given in EP 0 300 620 A1 describing so called "gel forming compositions" constituted of a alkenylsubstituted polyorganosiloxane containing hydrogen atoms bonded to some of the silicon atoms and a platinum catalysator.

Wacker SilGel 612 is a commercially available RTV-silicone system. It is a two component system. By varying the proportions between the two components A:B from 1.0:0.7 to 1.0:1.3 the softness and adhesion level of the formed gel can be varied.

Examples of further soft, skin friendly silicone gels that preferably can be used are NuSil MED-6340, NuSil MED3-6300, NuSil MED12-6300 from NuSil Technology, Carpintiera, Ga., USA and Dow Corning 7-9800 from Dow Corning Corporation, Midland, USA.

Also other soft, skin friendly adhesives might preferably be used in the present invention, for example hot-melts similar to Dispomelt® 70-4647 from National Starch and Chemical Company, Bridgewater, N.J., USA.

Figure 4:
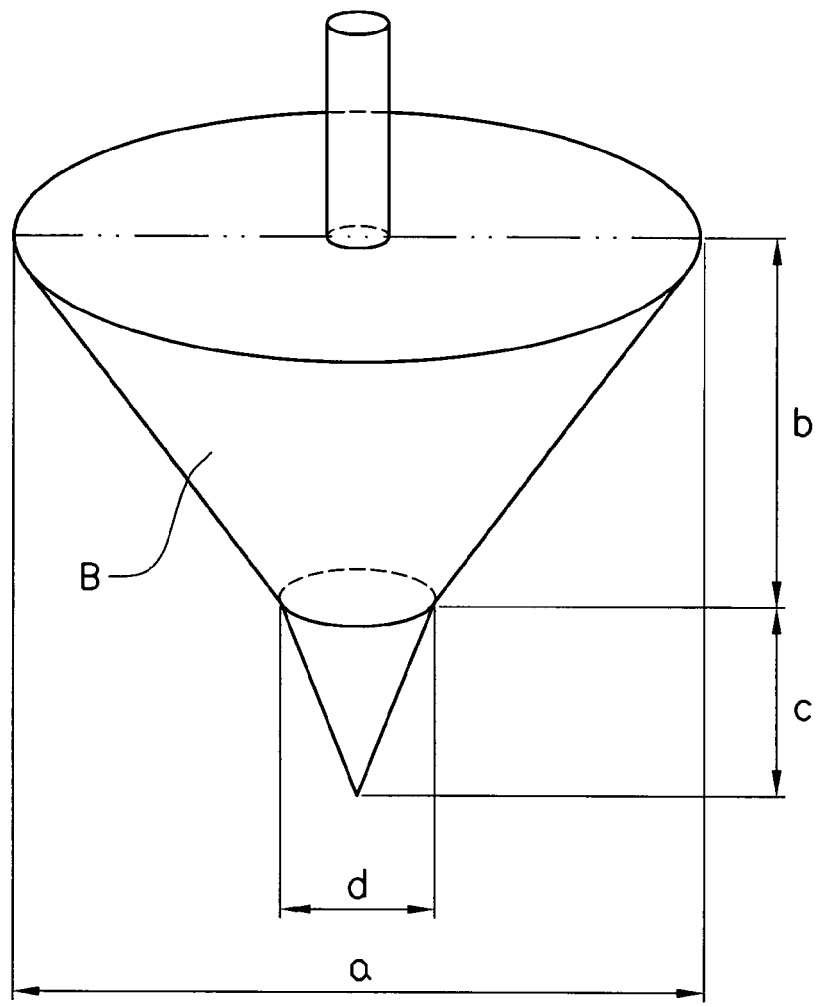
Figure 5:
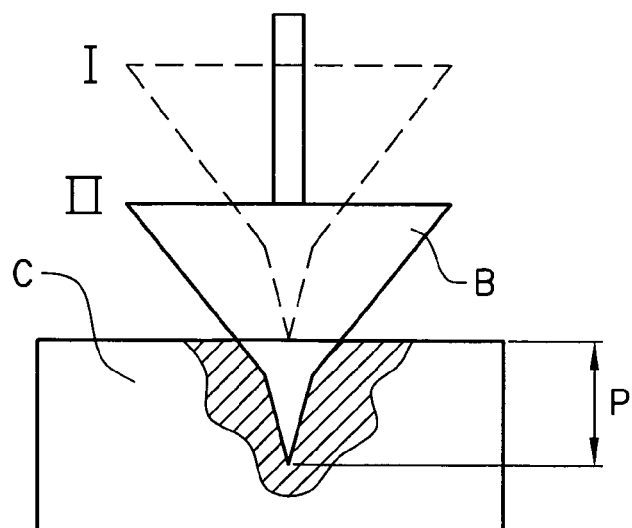

Preferred soft adhesives should preferably exhibit a softness that exceeds 10 mm measured by means of a method based on ASTM D 937 and ASTM D 51580. Certain deviations, as can be appreciated below, have been made. FIGS. 4 and 5 illustrate this modified method of measuring the softness of an adhesive by causing a cone B with a weight of 62.5 g to penetrate down by the effect of gravity into a 30 mm thick test piece C of the adhesive for which the softness is to be determined. The test piece is obtained by filling a cylindrical glass container having an internal diameter of 60 mm and an internal height of 35-40 mm, with adhesive to a depth of 30 mm. In the case of a silicone gel, it is necessary to fill a non-cured silicone prepolymer into the container, and then to cross-link it to a gel in the glass cylinder. The cone used is illustrated in FIG. 4 and has the following dimensions: a=65 mm, b=30 mm, c=15 mm and d=8.5 mm. In the performance of the method for measurement of the softness, the cone B is first lowered down into a position I, as illustrated with broken lines in FIG. 5 and in which the tip of the cone just touches the surface of the test piece C. The cone B is then released, so that it is able to penetrate down into the test piece C by the effect of gravity. The number of millimetres by which the tip B of the cone has penetrated into the test piece C after 5 seconds is measured and constitutes the penetration value P, the value of which is greater in proportion to the softness of the test piece. The penetration value P represents the softness index used in the present invention. A PNR 10 penetrometer supplied by Sommer & Runge KG, Germany is used in the performance of the method.

It has also been found the risk for leakage due to irregularities in the skin will be less the softer the adhesive and the higher the basis weight. It is therefore preferred that the softness of the adhesive is greater than 10 mm and the basis weight is at least 50 $g/m^2$.

The products proposed in the present invention can be supplied packed in sterile conditions, which means that the adhesives used in such cases must be capable of being sterilized, as must other components of such articles, of course.

The release layer is constituted by a plastic film, for example of polyethylene, having protrusions on the side thereof facing the adhesive layer 3.

The magnitude of the additional holding force created by the sub-pressure is dependent on the sub-pressure in the closed space and the open area of the first film layer 2, i.e. the sum of the areas of the openings 8, in the region delimited by the outer and inner perimeters of the compressible body 5. The sub-pressure is in turn dependent the amount of air being pressed out of the compressible body 5, in other words the difference between the volume of compressible body in uncompressed condition and its volume after having been pressed. The volume of said compressible body will vary depending on the magnitude of the desired sub-pressure and the size of the body.

The non-return valve 7 consists in the shown embodiment of a tube of flexible material with one end connected to the space between the first and second films 2,6 containing the compressible body 5, by a slit or the like in the second film 6. The opposite end of said tube, its free end, is connected to the atmosphere. The tube that the non-return valve 7 consists of, is in a relaxed condition collapsed so that the interior of the upper and lower sides of said tube abut each other so that no air can pass into the closed space containing the compressed body. However, by compressing said compressible body an over-pressure will be created in the closed space whereby air will flow out of said space via said slit or the like into the end of the tube. The over-pressure will press the abutting wall parts of the tube apart, thereby letting the air from the closed space out of the tube. When the pressure on the compressible body cease, this body will try to retain its relaxed shape thereby creating a sub-pressure in the closed space. A sub-pressure will then also occur in the tube and the atmospheric pressure will press the walls of the tube tightly together so that no air can flow into the closed space.

Other types of non-return valves than the described type or variants thereof can be used.

In an alternative (not shown) the non-return valve is present in a line leading from the closed spaced containing said compressible body to the surrounding atmosphere and the outer end of said line is connectable to a source of sub-pressure, which could be a manual or automatic pump. The sub-pressure will then be created by sucking air out of the closed space containing the compressible body by the aid of said pump. Also in this case the sub-pressure created will be dependent on the amount of air sucked out of said closed space. When designing the compressible body in the first embodiment it must be taken into account that the manual pressing on the compressible body probably will not result in a maximal compression of the body, i.e. there will be air left therein after the manual pressure has ceased, so that the volume of said body will be larger than what theoretically is necessary. In the second embodiment when the air is sucked out of the body by a source of sub-pressure, a maximal efficiency can be expected thereby allowing a theoretically optimal design of said body. A body of a smaller size can therefore be used in the second embodiment.

After creating a sub-pressure in the closed space containing the compressible body, the user attaches an ostomy bag to the upper side of component 1. It would then be difficult to manually press on the compressible body when the ostomy bag is attached to the component so it is essential that the skin-friendly adhesive really ensures that no air leak occur beneath the adhesive layer. In other words it is important that the adhesive has filled all unevenness in the skin. It is therefore preferred that the skin-friendly adhesive in layer 3 has a basis weight of 50 g/m² or more and a softness of 10 mm or more in order to minimise the risk for air to leak into the closed space.

In the second alternative using an external pump or the like, it is relatively easy to attach a pump or the like to the free end of the line in which the non-return valve is present even after attaching an ostomy bag to the component. The demand on the air-tightness of the adhesive is therefore less in the second embodiment than in the first embodiment.

The through-going openings 8 in the region delimited by the outer and inner perimeters of the compressible body 5 are in the disclosed embodiment arranged in a pattern of perforations evenly distributed in said region. However, an area of the first film 2 around the perimeter of hole 4 should be free of openings so that an annular area of adhesive without openings is present around hole 4.

A stiffening layer in the form of a frame extending along the edge portions of film layer 2 can optionally be releasably attached thereto for facilitate handling and application of component 1.

Figure 6:
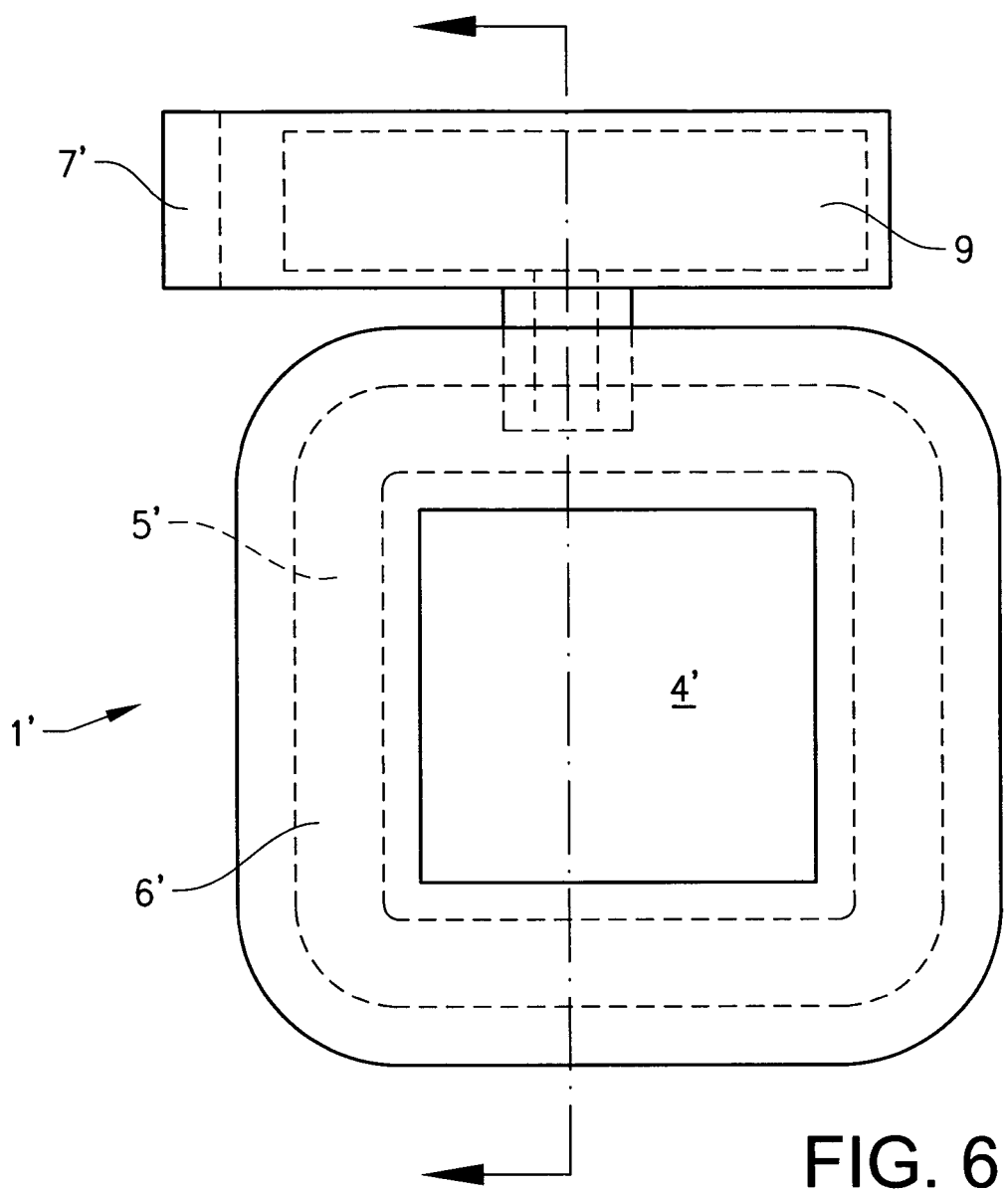
FIGS. 6 and 7 shows views similar to FIGS. 1 and 2 of a component according to a second preferred embodiment.
Figure 7:
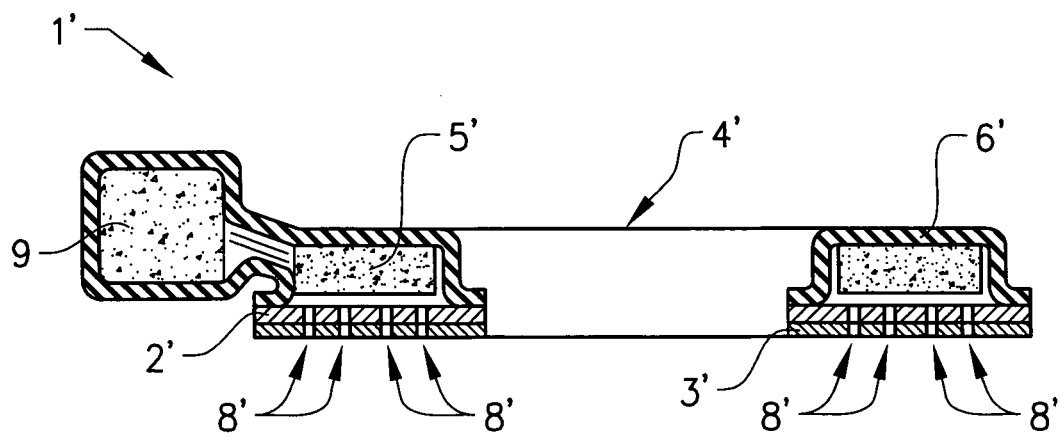

In FIGS. 6 and 7 a second embodiment of a component 1' according to the present invention is schematically shown. This embodiment differs from the embodiment shown in FIGS. 1-3 mainly in that a manual pump 9 is incorporated in the component 1'. Elements in the component 1' corresponding to similar elements in the component 1 according to FIGS. 1-3 are given the same reference numerals as in FIGS. 1-3 with the addition of a prime sign.

The pump 9 is preferably of a type comprising a body of a resilient, compressible foam material, a non-return valve 7' being present in the outlet from the pump. Such a pump is for example known from U.S. Pat. No. 3,572,340. Also other types of manual pumps, such as a bellows pump, can be used. A non-return valve is preferably also present in the line leading from the pump into the space containing the compressible body 5' in order to ensure that air is not pressed against the wound when said pump 9 is actuated.

It is of course possible to attach a wound dressing instead of a ostomy bag to a component according to the present invention, the wound pad of such a dressing being placed within the opening of the component. In a variant, the opening 4,4' inside the annular body 5,5' can be covered by one or both of the films 2,6,2',6' or by a separate piece of material and such a component can be placed over a wound dressing fitting into the space inside the annular body, the film, films or separate piece of material then pressing against the wound dressing.

Tests with a component according to FIGS. 6 and 7 but connected to an electrical pump has shown that the holding force on a moist Teflon® surface increased by 45% by application of a sub-pressure of 2.666 kPa (20 mmHg) and as much as 70% by application of a sub-pressure of 8 kPa (60 mmHg). The holding force on dry skin did also increase but not so significantly, 20% at 2.666 kPa and 30% at 8 kPa, respectively.

Bodies suitable for the present invention shall be able to create a subpressure of 0.665-78 kPa (5-400 mmHg), preferably 1.33-19.95 kPa (10-150 mmHg) and most preferably 1.33-10.64 kPa (10-80 mmHg).

The described embodiments can of course be modified without leaving the scope of invention. For example, a pump according to the second embodiment can be used in the first embodiment instead of disclosed non-return valve and vice versa. The openings in the region delimited by the outer and inner perimeters of the compressible body can have different shapes than circular, for example square, rectangular, diamond shape, arc-shaped, etc. Moreover, the openings do not have to be as numerous as in the pattern shown in FIG. 3 but can for example consist of two concentric rows of three arc-shaped openings, the openings in the outer row overlapping the openings in the inner row in the circumferential direction. Such openings will of course be larger than the openings 8 in order to maintain the desired open area of the first film layer in this region. The properties of the adhesive layer can also be varied in different regions thereof For example, the adhesive can be softer in the region delimited by the outer and inner perimeters of the compressible body than in the region surrounding the compressible body. The component can also have another shape than the disclosed essentially rectangular shape, for example a circular shape. Other types of adhesives than the adhesives mentioned in the description of embodiments can be used, but the use of soft adhesives is preferred. The scope of invention shall therefore only be restricted by the content of the enclosed patent claims.

The invention claimed is:

1. A component for securing attachment of a medical device to the skin of a patient, said component comprising a first plastic film coated with a skin-friendly adhesive on the lower side thereof, wherein the lower side faces the skin when the component is used, wherein an annular body of soft, compressible and elastic material having an inner and outer circumference is disposed between the first plastic film and a second plastic film, said first and second plastic films extending beyond the compressible body around the inner and outer circumferences thereof and are affixed directly to each other in parts extending around the inner and outer circumferences of the compressible body so that a closed space containing said compressible body is formed, said closed space being in contact with the surrounding atmosphere by a non-return valve such that when said compressible body is compressed, air is pushed out of said closed space through said non-return valve into the surrounding atmosphere, and wherein the first plastic film includes through-going openings in a region delimited by the compressible body.

2. The component according to claim 1, wherein said compressible body is made of polymer foam.

3. The component according to claim 2, wherein said compressible body is made of polyurethane foam.

4. The component according to claim 1, wherein said non-return valve consists of a tube of flexible material, the tube having an interior with upper and lower sides with one end connected to the space between the first and second films containing said compressible body and the opposite end connected to the atmosphere, said tube being collapsed in a relaxed condition so that the interior of the upper and lower sides of said tube abut each other in the relaxed condition but will be distanced from each other by an over-pressure created by compressing said compressible body.

5. The component according to claim 1, wherein a pump for creating sub-pressure is connected to the closed space containing the compressible body, the non-return valve being connected to the outlet of said pump.

6. The component according to claim 1, wherein said non-return valve is present in a line leading from the closed spaced containing said compressible body to the surrounding atmosphere, the outer end of said line being connectable to a source of sub-pressure.

7. The component according to claim 1, wherein the through-going openings in said region delimited by said compressible body are arranged in a pattern of perforations evenly distributed in said region.

8. The component according to claim 1, wherein the adhesive layer is a tacky silicone gel.

9. The component according to claim 1, wherein a layer of release material covers the adhesive layer before use of the component.

10. A medical device comprising a wound dressing attached to the component of claim 1.

11. A medical device comprising an ostomy bag attached to the component of claim 1.

* * * * *

UNITED STATES PATENT AND TRADEMARK OFFICE
CERTIFICATE OF CORRECTION

PATENT NO. : 8,545,469 B2  Page 1 of 1
APPLICATION NO. : 13/057571
DATED : October 1, 2013
INVENTOR(S) : Andresen et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 83 days.

Signed and Sealed this
Fifteenth Day of September, 2015

Michelle K. Lee
*Director of the United States Patent and Trademark Office*